United States Patent [19]

Kane et al.

[11] Patent Number: 5,681,532
[45] Date of Patent: Oct. 28, 1997

[54] OPTICAL SENSORS FOR THE MEASUREMENT OF OXYGEN

[75] Inventors: James Kane, N. Brunswick, N.J.; Roy Martin, Maple Grove; Anne Marie Schilling, Mahtomedi, both of Minn.

[73] Assignee: Optical Sensors, Incorporated, Eden Prairie, Minn.

[21] Appl. No.: 449,267

[22] Filed: May 24, 1995

Related U.S. Application Data

[62] Division of Ser. No. 120,593, Sep. 13, 1993, Pat. No. 5,462,880.

[51] Int. Cl.[6] ............... G01N 21/64; G02B 1/08
[52] U.S. Cl. .................. 422/82.06; 422/82.07; 422/82.08; 422/82.11; 422/83; 250/459.1
[58] Field of Search ............ 422/82.06, 82.07, 422/82.08, 82.11, 83; 250/459.1

[56] References Cited

U.S. PATENT DOCUMENTS

| | | | |
|---|---|---|---|
| 3,475,384 | 10/1969 | Trischler | 260/77.5 |
| 3,574,770 | 4/1971 | Paine | 260/61.5 |
| 3,642,705 | 2/1972 | Zollinger | 260/77.5 |
| 3,671,497 | 6/1972 | Low et al. | 260/77.5 |
| 3,755,265 | 8/1973 | Fletcher et al. | 260/77.5 |
| 3,810,874 | 5/1974 | Mitsch et al. | 260/77.5 |
| 4,577,109 | 3/1988 | Hirschfeld | 422/82.07 |
| 4,785,814 | 11/1988 | Kane | 422/82.07 |
| 4,842,783 | 6/1989 | Blaylock | 422/82.07 |
| 4,849,172 | 7/1989 | Yafuso et al. | 422/55 |
| 5,030,420 | 7/1991 | Bacon et al. | 422/82.07 |
| 5,043,286 | 8/1991 | Khalil et al. | 436/136 |
| 5,094,959 | 3/1992 | Allen et al. | 436/172 |
| 5,108,932 | 4/1992 | Wolfbeis | 436/174 |
| 5,308,771 | 5/1994 | Zhou et al. | 436/39 |
| 5,405,975 | 4/1995 | Kuhn et al. | 549/347 |
| 5,436,167 | 7/1995 | Robillard | 436/165 |

FOREIGN PATENT DOCUMENTS

| | | |
|---|---|---|
| 2 132 348 | 7/1984 | United Kingdom . |
| WO 92/12424 | 7/1992 | WIPO . |

OTHER PUBLICATIONS

Seitz, "Chemical Sensors Based on Fiber Optics," *Anal. Chem.* (1984) 56(1):17A–34A.

*Primary Examiner*—Nina Bhat
*Attorney, Agent, or Firm*—Reed & Robins

[57] ABSTRACT

A ratiometric method for using optical sensors is provided to measure dissolved oxygen in a fluid sample. The sensor is formulated so as to contain an oxygen permeable membrane of a cured perfluorinated urethane polymer and, incorporated therein, an oxygen-sensitive indicator component and a reference dye component. The emission spectrum from the indicator component is calibrated by comparison with that of the reference dye, which is substantially less sensitive to oxygen-quenching and which has a photodecomposition rate similar to the indicator component. Methods for making and using the membrane and sensor are provided as well.

10 Claims, 6 Drawing Sheets

5,681,532

1

OPTICAL SENSORS FOR THE MEASUREMENT OF OXYGEN

CROSS-REFERENCE TO RELATED APPLICATIONS

This is a divisional of U.S. Ser. No. 08/120,593, filed Sep. 13, 1993, now U.S. Pat. No. 5,462,880.

TECHNICAL FIELD

The present invention relates generally to methods of using optical sensors for measuring dissolved oxygen. More particularly, the invention relates to a novel ratiometric method of measuring dissolved oxygen using an optical sensor system containing an oxygen-permeable membrane composition of a fluorescent hydrophobic urethane copolymer, an oxygen indicator component and a reference dye component. The invention additionally relates to fluorescent polymeric compositions for use in an optical oxygen sensor, to membranes which may be manufactured therefrom, and to methods of making these sensors and membranes.

BACKGROUND

Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location without requiring electrical communication with the remote location. Structures, properties, functions and operational details of fiber optic chemical sensors can be found in U.S. Pat. No. 4,577,109 to Hirschfeld, U.S. Pat. No. 4,785,814 to Kane, and U.S. Pat. No. 4,842,783 to Blaylock, as well as Seitz, "Chemical Sensors Based on Fiber Optics," *Analytical Chemistry*, Vol. 56, No. 1, January 1984, each of which is incorporated by reference herein.

Publications such as these generally illustrate that is it known to incorporate a chemical sensor into a fiber optic waveguide, an electrochemical oxygen sensor or the like, in a manner such that the chemical sensor will interact with the analyte. This interaction results in a change in optical properties, which change is probed and detected through the fiber optic waveguide or the like. These optical properties of chemical sensor compositions typically involve changes in colors or in color intensities. In these types of systems, it is possible to detect particularly minute changes in the parameter or parameters being monitored in order to thereby provide especially sensitive remote monitoring capabilities.

Chemical sensor compositions that are incorporated at the distal end of fiber optic sensors are often configured as membranes that are secured at the distal tip end of the waveguide device or optrode. Sensors of this general type are useful in measuring gas concentrations such as oxygen and carbon dioxide, monitoring the pH of a fluid, and the like. Ion concentrations can also be detected, such as potassium, sodium, calcium and metal ions.

A typical fiber optic oxygen sensor positions the sensor material at a generally distal location with the assistance of various different support means. Support means must be such as to permit interaction between the oxygen indicator and the substance being subjected to monitoring, measurement and/or detection. With certain arrangements, it is desirable to incorporate membrane components into these types of devices. Such membrane components must possess certain properties in order to be particularly advantageous. Many membrane materials have some advantageous properties but also have shortcomings. Generally speaking, the materials must be biocompatible, hemocompatible for use in the bloodstream, selectively permeable to oxygen molecules, and of sufficient strength to permit maneuvering of the device without concern about damage to the oxygen sensor.

It is also desirable to have these membrane materials be photocurable (such that curing is neater, can be done more rapidly, on a smaller scale, and directly on the optical fiber), resistant to shear forces e.g., as present in a bloodstream), and compatible with different substrates, such that there is a choice of fiber optic materials which can be used to fabricate the sensor. It is also preferred, clearly, that a signal of sufficient intensity be produced, such that measurement is as accurate as is reasonably possible. The optical oxygen sensors which are currently available commercially are frequently inadequate with regard to one or more of the aforementioned criteria.

One principal problem with commonly used chemical indicators is that they are photolabile. The radiant energy in light induces photochemical reactions which hasten the decomposition of the indicators and thereby abbreviate their useful lives. This photodecomposition results in a coordinate signal decay referred to as photodrift.

Various approaches have been used to solve the problem of photodrift. Some environmentally sensitive dyes have a portion of their visible spectrum which shows either a total environmental insensitivity (isobestic point) or a relative insensitivity. This property can be used to advantage by ratioing the signal from the environmentally sensitive portion of a indicator's spectrum to that from the isobestic point. The ratio of the signals should be invariant as the indicator molecule photodecomposes and the absolute signal value decays. This principle has been employed to ratio the signals obtained from fluorescein when measuring pH.

An alternate method of contending with the problem of photodrift involves the use of a separate internal reference dye which is environmentally insensitive, but photodecomposes at the same rate as the indicator dye. When an internal reference dye is incorporated into the optical sensor, the signal from the environmentally sensitive dye may be calibrated by comparison with that from the insensitive dye. Due to the similarity of the decay rates of the indicator dye and the reference dye, the ratio of the signals should not vary as the two dyes photodecompose.

In addition to the problem of photodrift, the photochemical reactions incident to exposure to light result in the ultimate decomposition of the organic dyes used as chemical sensors. The use of a system employing a method of ratioing the signals from indicator and reference dyes extends the intervals between which the sensor needs to be recalibrated to operate with accuracy and precision, i.e., to yield $O_2$ values which are within approximately 10% of the true $O_2$ value.

By irradiating with light of a specific wavelength, more than one specific wavelength, or a range of wavelengths, which may or may not be the wavelength of maximum absorption, while measuring the fluorescence emission at specific wavelengths, which may or may not be the wavelength of maximum emission intensity, or a range of wavelengths in conjunction with specific light filtering devices, so as to discern the fluorescence emission of the indicator dye from that of the reference dye, calibration of the emission signal of the indicator dye may be effected by ratioing it to that of the reference dye. This results in a signal ratio which is sensitive to the analyte of interest and less sensitive to the effects of exposure to light (photodecomposition of the signal, photodecomposition of the compound) than a single indicator dye sensor composition, and a prolonged useful life of the oxygen sensor.

Organometallic transition complexes which are readily quenched experience photodecomposition rates which can be influenced by the support means in which they are entrapped for use as a chemical sensor. However, these complexes have no portion of their fluorescence spectrum which are environment insensitive. While they are not amenable to use in a single-dye chemical sensor composition ratioing system, they may be employed in conjunction with a fluorescent organic dye with the requisite decay rate and analyte insensitivity to ratio the emission signals therefrom.

She present invention is addressed to a novel ratiometric method of measuring dissolved oxygen in a fluid using optical sensors and fluorescent polymer compositions which have been found to be particularly suitable for use as membranes and membrane-like components in an optical oxygen sensor and which provide for optical sensors which address each of the above-mentioned concerns. That is, optical sensors as provided herein display excellent adhesion to different types of substrates, eliminating in some cases the need to silanize the substrate surface, provide for superior signal intensity, are quite hemocompatible relative to prior art compositions, are rapidly cured with light, are resistant to shear forces such as those present in flowing blood and allow for the ratiometric comparison of signals from environmentally sensitive and insensitive molecules which have the same decay rates.

Overview of Related Art

The following references relate to one or more aspects of the present invention. The first reference relates generally to calibrating techniques. The subsequent three references relate to optical oxygen sensors. The final three references relate to techniques of calibrating fiber optic oxygen sensors.

U.S. Pat. No. 4,792,689 to Peterson describes an improved fiber optic sensor in which a method is provided for correcting for common path variation in intensity. The method involves passing two wavelengths of light through a single sample, one of which results in analyte-sensitive fluorescence emission and the other of which results in analyte nonsensitive emission.

U.S. Pat. No. 4,861,727 to Hauenstein et al. describes an oxygen sensor in which oxygen-quenchable luminescent lanthanide complexes are employed as indicators.

U.S. Pat. No. 5,043,286 to Khalil et al. describes a method and apparatus for measuring oxygen concentration in a fluid. The method involves the use of a luminescent, fluorinated platinum or palladium complex as the oxygen indicator.

U.S. Pat. No. 5,057,277 to Mauze et al. describes an organosilicon composition for use in chemical sensing. In one embodiment, a silicone matrix having a radiative material such as a ruthenium dye incorporated therein is used to determine the concentration of oxygen in an analyte.

U.S. Pat. No. 5,094,959 to Allen et al. describes an oxygen sensor in which a single indicator species is used as both the indicator and the reference element.

U.S. Pat. No. 5,094,958 to Klainer and Goswami describes a method for "self-calibrating" an oxygen sensor. In a primary embodiment, the method involves the use of an indicator material which produces two distinct analyte-specific phosphorescence emissions and two distinct analyte-nonspecific fluorescence emissions which are ratioed to obtain a measurement signal that is independent of external factors such as degradation, leaching, or the like.

U.K. Patent Application No. 2,132,348 to Bacon et al. describes an oxygen sensor in which the gas sensitive indicator component is a luminescent organometallic complex.

Lee et al., Anal. Chem. 59(2):279–283 (1987), discloses optical sensors which are internally calibrated by virtue of a single reagent which gives rise to two luminescence bands, one of which is quenched by oxygen and the other of which is not.

SUMMARY OF THE INVENTION

Accordingly, it is a primary object of the invention to address the above-mentioned needs in the art, by providing a method for measuring dissolved oxygen in a fluid using an optical sensor which has improved photostability, sensitivity, resolution, solvent resistance, and resistance to shear.

It is another object of the invention to address deficiencies in the art by providing such a method in which the optical sensor is formulated with a cured perfluorinated urethane polymer, an oxygen-sensitive indicator component and a reference dye component, and wherein the oxygen-sensitive indicator is a ruthenium indicator and the reference dye is a perylene derivative.

It is yet a further object of the invention to provide such a method wherein the apparent quantity of oxygen present in the fluid is corrected for variation in external factors by determining the ratio of the oxygen indicator emission signal to the reference dye emission signal.

It is another object of the invention to provide an optical oxygen sensor which contains a membrane of a cured perfluorinated urethane polymer, an oxygen-sensitive indicator component and a reference dye component.

It is still another object of the invention to provide such a sensor in which the perfluorinated urethane polymer comprises a perfluorinated polyurethane acrylate.

It is a further object of the invention to provide a method of making such an optical oxygen sensor by polymerizing a precursor to a perfluorinated urethane polymer on a fiber optic tip.

It is yet another object of the invention to provide an oxygen-permeable membrane for use in such a sensor, which comprises a polymeric matrix of a cured perfluorinated urethane polymer, and, incorporated therein, an oxygen-sensitive indicator component and a reference dye component.

It is a further object of the invention to provide such a membrane in which the perfluorinated urethane polymer comprises a perfluorinated polyurethane acrylate.

Additional objects, advantages and novel features of the invention will be set forth in part in the description which follows, and in part will become apparent to those skilled in the art upon examination of the following, or may be learned by practice of the invention.

In one aspect, a method for measuring dissolved oxygen dissolved in a fluid is provided, wherein the method comprises:

(a) providing an optical sensor comprising an optical waveguide having a distal end portion for measuring dissolved oxygen in a fluid, e.g., a bloodstream or the like, and a proximal end portion for communication with means for receiving a signal from the distal end portion, and wherein the distal end portion has an oxygen sensor means comprising a cross-linked oxygen-permeable membrane of a cured perfluorinated urethane polymer and, incorporated therein, an indicator composition of an oxygen indicator and a reference dye, wherein the oxygen indicator provides for an analyte-sensitive fluorescence emission signal, and wherein the reference dye provides for an analyte-insensitive fluorescence emission signal;

(b) contacting the fluid sample with the distal end portion of the optical sensor;

(c) exciting the indicator composition with a radiation of a first wavelength, to produce an oxygen indicator emission signal at a second wavelength and a reference dye emission signal at a third wavelength;

(d) calculating the apparent quantity of oxygen present in the fluid sample from the oxygen indicator emission signal; and (e) correcting the apparent quantity of oxygen present for variations resulting from external factors, by determining the ratio of the oxygen indicator emission signal to the reference dye emission signal.

In another aspect, an optical sensor is provided for measuring dissolved oxygen, which comprises an optical waveguide having a distal end portion for monitoring oxygen within a fluid, e.g., a bloodstream or the like, and a proximal end portion for communication with means for receiving a signal from the distal end portion, and wherein the distal end portion has an oxygen sensor means comprising a cross-linked oxygen permeable membrane as summarized above and as will be described in detail below.

In another aspect, a method is provided for making the aforementioned optical sensor. In a preferred embodiment, the method involves polymerization of a photocurable polymeric precursor on the fiber optic tip, by irradiating the precursor-coated tip through the optical fiber. In another embodiment, polymerization of a perfluorinated urethane polymer precursor may be effected by contacting the precursor-coated tip with a cross-linking agent in solution or the like.

In still another aspect, a cross-linked oxygen permeable membrane useful in optical oxygen sensors is provided, wherein the membrane comprises a polymeric matrix of a cured perfluorinated urethane polymer, and, incorporated therein, an oxygen-sensitive indicator component and a reference dye component, as will be described in detail herein. In a preferred embodiment, the perfluorinated urethane polymer is a perfluorinated polyurethane acrylate which comprises a perfluorinated polyurethane acrylate precursor cross-linked with a cross-linking agent, the oxygen indicator component is ruthenium indicator and the reference dye component is a perylene derivative.

DETAILED DESCRIPTION OF THE INVENTION

Figure 1:
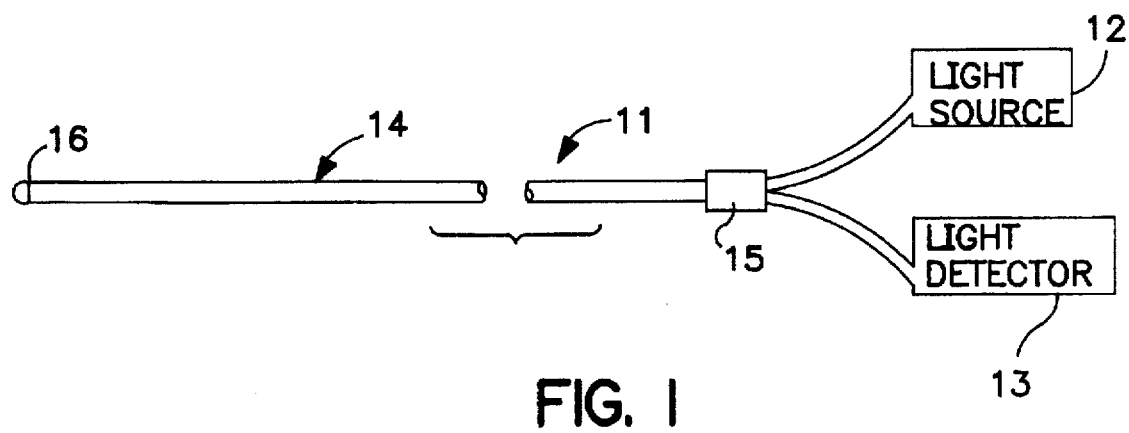
FIG. 1 is a generally schematic view of a chemical sensor device according to the present invention which is incorporated in a fiber optic oxygen sensor device.
Figure 2:
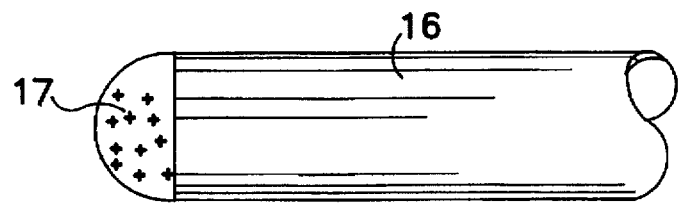
FIG. 2 is an enlarged, detail and generally schematic view of the distal end portion of an oxygen sensor device generally in accordance with FIG. 1 and incorporating a monolithic cross-linked fluorocarbon polymer according to the present invention.

Before the present compositions, membranes, sensors and methods of manufacture are disclosed and described, it is to be understood that this invention is not limited to specific sensor formats, specific membrane compositions, or particular cross-linking agents or curing processes, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an oxygen indicator" includes mixtures of two or more oxygen indicators, reference to "a perfluorinated urethane polymer" includes mixtures of such polymers, reference to "a precursor" includes mixtures of two or more precursors, and the like.

In describing and claiming the present invention, the following terminology will be used in accordance with the definitions set out below.

The term "oxygen indicator" is intended to mean an environmentally sensitive, organic and/or organometallic chemical compound which,. when exposed to an appropriate wavelength of light, emits a measurable fluorescence signal which is sensitive to (i.e., quenched by) the oxygen to which it is exposed.

The term "reference dye indicator" is used herein to mean an organic and/or organometallic chemical compound which, when exposed to an appropriate wavelength of light, emits a measurable fluorescence signal which is substantially insensitive to (i.e., not significantly quenched by) the analyte of interest, and which displays a photodecomposition rate which is approximately the same as that of a selected environmentally sensitive indicator dye.

The term "polymer" as used herein is intended to include both oligomeric and polymeric materials, i.e., compounds which include two or more monomeric units. Similarly, the term "perfluorinated polyether" linkage is intended to mean a linkage containing at least two perfluorinated ether monomer units, i.e., ether monomer units in which each hydrogen atom normally present has been replaced by a fluorine atom.

The term "urethane" is used herein in its conventional sense to denote organic compounds containing a recurring —O—(CO)—NH— linkage. The term "urethane acrylate polymer" is intended to mean a urethane polymer derived from polymerization of a urethane oligomer having acrylate termini —O—(CO)—CH=CH$_2$.

The term "precursor" is used herein to mean a compound which when polymerized and/or cross-linked will give rise to a desired polymer. The term "photodecomposition" is used herein to refer to the chemical decomposition, by photolysis processes, which accompanies the illumination of material. This is distinguishable from "photodecay," the nondestructive process in which a fluorescent molecule in the excited state decays to a lower energy state with the concomitant emission of light.

The "Stern Volmer constant" ($K_{sv}$) is used herein as it is normally defined, i.e., $$Io/I = 1 + K_{sv}([O_2])$$

where "Io" represents the fluorescence at 0% oxygen concentration, "I" represents the measured fluorescence when oxygen is present.

The "drift limit" is used herein as it is normally defined, i.e., $$\text{Drift limit} = DL = \frac{1 + K_{sv}(150)}{1 + K_{sv}(165)}.$$

The drift limit thus signifies the fraction of the initial signal which can be lost through drift and still remain within approximately 10% error at 150 mm Hg.

The "drift rate" is used herein as it is normally defined, i.e., $$\text{Drift rate} = DR = \frac{\text{signal}(t=0) - \text{signal}(\text{end burn-in})}{\text{signal}(t=0)} \div \text{hours burn in}.$$

The drift rate is thus the fractional signal a sensor loses per hour during defined burn-in conditions; the units are in % signal lost per hour. "Fractional drift" $D_f$ is defined as 1−(DR).

The term "New O$_2$/Hour" is the predicted oxygen given by a sensor in 150 mmHg after 1 hour of use, and is calculated as follows:

$$\text{New O}_2/\text{Hour} = \frac{1 + K_{sv}(150)}{D_f \cdot K_{sv}} - \frac{1}{K_{sv}}.$$

In describing chemical compounds herein, the term "lower alkyl" is used in its conventional sense to mean an alkyl group of 1 to 6 carbon atoms, e.g., methyl, ethyl, n-propyl, isopropyl, n-butyl, isobutyl, t-butyl, and the like. "Lower alkylene" refers to a difunctional saturated branched or unbranched hydrocarbon chain containing from 1 to 6 carbon atoms, and includes, for example, methylene (—CH$_2$—), ethylene (—CH$_2$CH$_2$—), propylene (—CH$_2$—CH$_2$—CH$_2$—), and the like. The term "alkylarylene" refers to a difunctional hydrocarbon moiety containing 1 or 2 monocyclic aromatic moieties, either unsubstituted phenyl rings or containing one to four substituents such as lower alkyl, halogen, nitro, or the like. "Alkylarylene" linking groups may also contain lower alkylene spacers adjacent the aromatic rings, in which some or all of the hydrogen atoms normally present may be replaced with fluorine atoms.

The polymeric compositions which are used to formulate the oxygen permeable membrane of the invention are cured perfluorinated urethane polymers; the membrane itself comprises a matrix of such a polymer and, incorporated in the matrix, an oxygen-sensitive indicator component and a reference dye component. The cured perfluorinated urethane polymers are typically perfluorinated urethane polymer precursors cross-linked with a cross-linking agent. Generally, such precursors have the structural formula

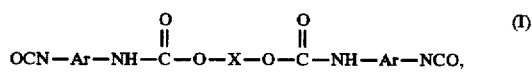

wherein Ar is a monocyclic aromatic moiety and X is a perfluorinated polyether linkage containing approximately 2 to 100, preferably 10 to 50, most preferably 30 to 45, recurring perfluorinated monomer units having the structure (—CF$_2$O—), (—CF$_2$CF$_2$O—), or combinations thereof. Hydrophobicity may easily be modulated by varying the number of perfluorinated ether units contained within the moiety X. Preferably, Ar is phenyl, either unsubstituted or substituted with one to four substituents which are selected so as not to interfere with polymerization or use of the cured polymer in the oxygen sensor; such substituents include, for example, lower alkyl (C$_1$–C$_6$), halogen, nitro, and the like. Hydrophobicity may easily be modulated by varying the number of perfluorinated ether units contained within the moiety X.

The precursor of Formula (I) may be cross-linked using water or an organic diol HO—R—OH wherein R is a hydrocarbon substituent of about 2 to 20 carbon atoms, and in which some or all of the hydrogen atoms normally present have been replaced with fluorine atoms. Preferably, R is an alkylene linking group, i.e., an alkylene linking group containing from about 1 to 6 carbon atoms, or an alkylarylene linking group containing one or two monocyclic aromatic moieties and, depending on the number of aromatic moieties, two or three lower alkylene spacer groups, again, in which some or all of the hydrogen atoms normally present have been replaced with fluorine atoms. Exemplary organic diols include bisphenol A and hexafluorobisphenol A.

In a preferred embodiment, the precursor of Formula (I) is converted to a perfluorinated urethane acrylate precursor prior to curing, by replacing the terminal isocyanate moieties —N=C=O with acrylate termini —NH—COO—(CH$_2$)$_n$—(CO)—CH=CH$_2$ where n is typically in the range of 1 to about 6. This may be effected by reacting the diisocyanate precursor (I) with, for example, hydroxymethylmethacrylate (in which case n is 1), hydroxyethylmethacrylate (in which case n is 2), or the like. The perfluorinated urethane acrylate precursor so provided, having the structural formula

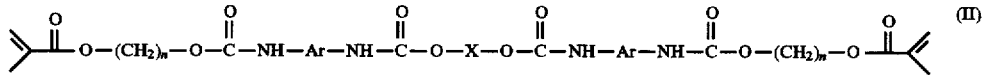

may then be cured in the presence of a suitable photoinitiator or photocatalyst using radiation. In a variation on this embodiment, the diisocyanate-terminated precursor of Formula (I) may be reacted with virtually any compound having a hydroxy terminus and a vinyl terminus, typically containing about 2 to 10 carbon atoms, to provide a vinyl-terminated precursor and to enable cross-linking.

Suitable photoinitiators for carrying out the cross-linking in the aforementioned case, i.e., to cure the perfluorinated urethane acrylate precursor of Formula (II), are radical photoinitiators that are well-known to those skilled in the art. Examples of such photoinitiators include 2-hydroxy-2,2-dialkyl acetophenones, α-alkoxy deoxybenzoins, α,α-dialkoxy deoxybenzoins, α,α-dialkoxy acetophenones, benzophenones, thioxanthones, benzils, and other compounds identified by H. J. Hageman et al., "Photoinitiators and Photocatalysts for Various Polymerisation and Crosslinking Processes," in Radiation Curing of Polymers II, ed. D. R. Randell (The Royal Society of Chemistry, 1991), at pp. 46–53, cited supra. The disclosure of the aforementioned reference is incorporated by reference herein.

In another embodiment, the diisocyanate-terminated precursor of Formula (I) is converted to an epoxy-terminated precursor having the formula

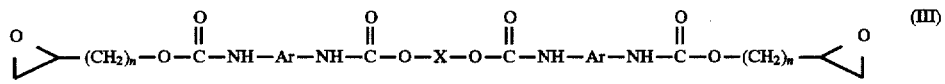

wherein Ar, X, and n are as defined above. This conversion may be readily effected by reaction of the precursor of Formula (I) with two equivalents of a compound having the structural formula

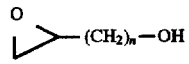

(i.e., glycidol when n is 1). This epoxy-terminated compound may then be cured with radiation in the presence of a cationic photoinitiator, e.g., a sulfonium salt, an organometallic complex such as that manufactured under the name Irgacure® by Ciba-Geigy Corporation, or the like.

One of the advantages of fabricating optical oxygen sensors with the aforementioned polymer compositions is that a cross-linking agent is generally not required. Conventional systems typically require a very high level of cross-linking agent.

In formulating the oxygen permeable membrane, it is preferred that the above-described cross-linking reaction occur in the presence of the oxygen-sensitive indicator component and the reference dye component which will then be incorporated into the polymeric matrix which serves as the membrane. The oxygen-sensitive indicator and the reference dye will generally be physically entrapped within the polymeric matrix, but it may also be covalently bound thereto.

The oxygen-sensitive indicator is typically an inorganic complex which is a luminescent material quenchable by the oxygen. Examples of suitable oxygen-sensitive indicators useful for oxygen determination may be found in U.K. Patent No. 2,132,348, cited supra, and include complexes of ruthenium (II), osmium (II), iridium (III), rhodium, rhenium, and chromium (III) with 2,2'-bipyridine, 1,10'-phenanthrolene, 4,7-diphenyl-1,10-phenanthrolene, 4,7-dimethyl-1,10-phenanthrolene, 4,7-disulfonated-diphenyl-1,10-phenanthrolene, 2,2'-bi-2-thiazoline, 2,2'-bithiazole, 5-bromo-1,10-phenanthrolene, and 5-chloro-1,10-phenanthrolene, and complexes of VO (II), Cu (II), platinum (II), and zinc (II) with porphyrin, etioporphyrin, tetraphenylporphyrin, mesoporphyrin IX dimethylester, protoporphyrin IX dimethylester and octaethylporphyrin. Preferred oxygen-sensitive indicators for fabricating oxygen optical sensors are ruthenium complexes, most preferred is tris(4,7-diphenyl-1,10-phenanthroline)ruthenium(II) chloride.

The reference dye is typically an organic luminescent material which is relatively unquenchable by oxygen (i.e., has a Stern Volmer constant $K_{sv}$ which is substantially smaller than that of the oxygen-sensitive indicator; in general, the $K_{sv}$ of the reference dye should be at least 0.05 less than that for the oxygen-sensitive indicator), has a fluorescence emission spectrum which can be readily discerned from that of the oxygen indicator dye and has a relatively stable photodrift rate (typically within about 1% when measured at 150 mm Hg) that is closely matched to that of the oxygen-sensitive indicator. Examples of reference dyes include polynuclear aromatic compounds, such as perylene derivatives, fluorescein and fluorescein derivatives such as carboxyfluorescein, hydroxypyrene trisulfonic acid, dichlorofluorescein, and the like. Preferred examples of such reference dyes are N,N'-bis(2,5-di-tert-butylphenyl)-3,4,9,10-perylenecarboximide and N,N'-bis(2,6-xylidyl)-3,4,9,10-perylenecarboximide (DXP).

The cross-linking reactions which give rise to the oxygen permeable membrane are preferably carried out on the fiber substrate. In a preferred embodiment, the precursor is photocurable and is cross-linked on the fiber substrate using radiation transmitted through the fiber. Alternatively, the membrane may be prepared separately and deposited on the surface of the optical fiber; in such instances, it is typically necessary to prime the fiber surface prior to deposition of the sensing membrane thereonto. An example of a suitable glass primer is γ-methacryloxypropyl trimethoxysilane. Alternatively, the distal tip of the fiber may be dipped into a solution of the precursor, the oxygen-sensitive indicator and the reference dye, and taking suitable steps to cure and cross-link the solution. Once cured, the oxygen sensor thus formed may be cleaned of residual unreacted monomer by soaking in an innocuous solvent such as dimethylsulfoxide or buffer/water. The present invention, however, minimizes the potential for unreacted monomer and rinsing may be a superfluous step.

The polymer composition—i.e., the cross-linked perfluorinated urethane polymer-will typically represent on the order of 80 to 99 wt. % of the oxygen permeable membrane, more typically 95 to 99 wt. % of the membrane. Any photoinitiator used will be present at customary levels, typically around 1-2 wt. % of the membrane. The oxygen-sensitive indicator and reference dye will generally represent on the order of 0.03–1.0 wt. % of the membrane.

Perfluorinated urethane polymers and optical sensors formulated with such polymers are described in detail in commonly assigned, copending U.S. patent application Ser. No. 07/911,175, entitled "Cross-Linked Gas Permeable Membrane of a Cured Perfluorinated Urethane Polymer, and Optical Gas Sensors Fabricated Therewith," filed Aug. 12, 1992 and incorporated herein by reference. Those skilled in the art who would like further information concerning fiber optic oxygen sensors formulated with perfluorinated urethane polymers are referred to the aforementioned patent application for additional detail.

FIG. 1 shows a typical fiber optic oxygen sensor arrangement. The illustrated device 11 includes a light source 12 for directing probe radiation into the device, as well as a light detector 13 for sensing and detecting radiation from the device. Device 11 includes one or more optical fibers 14 that are joined to light source 123 and to light detector 13 through a suitable junction assembly 15 at a location which is proximal of the distal end portion 16 of the optical fiber 14. As is generally known, each optical fiber 14 includes a core surrounded by a cladding or covering.

Distal end portion 16 has a distal tip 17 which is a membrane of a cross-linked perfluorinated urethane polymer matrix, and, incorporated therein, an oxygen-sensitive indicator and a reference dye as described above. The oxygen-sensitive indicator enables the matrix to undergo a known change in color, color intensity or other property, which change is observed by the light detector 13 in a manner generally known in the art.

Figure 3:
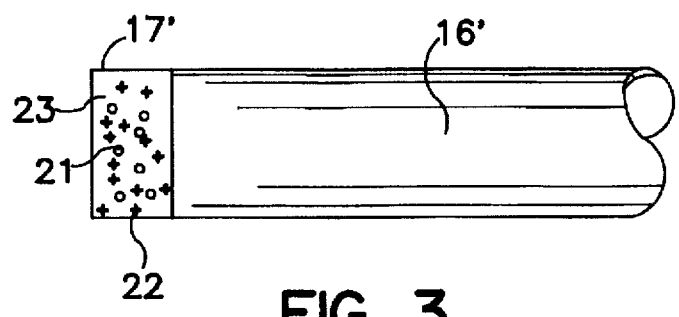
FIG. 3 is a view similar to FIG. 2 but illustrating a composite membrane arrangement.

With the embodiment illustrated in FIG. 3, a distal end portion 16' has a distal tip 17'. The tip 17' is a composite membrane suitable for multifunctional monitoring, such as for monitoring pH conditions or the like and oxygen concentrations. Microparticles 21 of a polymer matrix comprising a perfluorinated urethane polymer, an oxygen-sensitive indicator and a reference dye are included within the composite membrane at the distal tip 17'. Also included are other indicator components 22 such as fluorescent pH indicators. Both the oxygen sensor microparticles 21 and the other indicators 22 are encapsulated within a known type of oxygen and ion permeable hydrophilic polymer 23 which provide needed support for the microparticles therewithin.

Examples of suitable fiber substrate materials include glass, plastic, glass-on-glass and plastic-clad glass fiber waveguides. A critical characteristic of optical fibers is attenuation of the optical signal. Thus, glasses which contain unacceptable levels of transition-metal impurities when prepared from naturally occurring materials lead to high absorption losses. High silica fibers of acceptable quality can be prepared from purified starting materials (e.g., silicon tetrachloride and germanium tetrachloride) using conventional glass-melting techniques of melting, fining and drawing into fibers. In order to promote adhesion of the membrane to the fiber, the surface of the tip of the fiber substrate may be silanized, such as with γ-methacryloxypropyl trimethoxysilane as primer, as discussed above.

As noted earlier, the primary utility of the present invention is in the detection and measurement of dissolved oxygen in the bloodstream. However, the membrane and sensor of the invention may also be used in a variety of other contexts, e.g., for on-line sensing in a flowing fluid stream.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE 1

The objective of this example was to prepare a radiation-curable fluoropolyurethane for fabricating an $H_2O$ and $H^+$ impermeable membrane with good elastomeric properties. A difunctional, isocyanate-terminated fluorinated polyether having an equivalent weight of approximately 1500 (Fluorolink™ B, obtained from Ausimont, Morristown, N.J.) was used as the polymeric precursor. The reactions which were carried out (1) replaced the diisocyanate termini of the precursor with acrylate moieties, thereby providing a photocurable compound, and (2) cured this latter acrylate-terminated compound, as follows.

Five g of Fluorolink™ was weighed out and 0.43 g of dry hydroxyethylmethacrylate (HEMA) (obtained from Aldrich Chemical Company, Inc., Milwaukee, Wis.), which had been stored over 4Å molecular sieves, was added to the Fluorolink™ B. The reaction was permitted to proceed at room temperature uncatalyzed. After 1 hour, no apparent exotherm occurred. The reaction was incubated at approximately 20° C. for 18 hours. At that time, it was found that the preparation had not cured; accordingly, 5 μl dibutyltin dilaurate (obtained from Air Products and Chemicals under the name T-12) catalyst was added, and the preparation bubbled slightly.

The acrylate urethane was found to be soluble in Freon 113 trichlorotrifluoroethane; 5 μl of the photoinitiator Irgacure® 500 (Ciba-Geigy) was added, and the polymer solution was thus cured under a stream of $N_2$. The structure of the polymer was verified using infrared spectroscopy.

EXAMPLE 2

The objective of this example was to prepare an oxygen sensor by dissolving an oxygen-sensitive indicator and a reference dye in a cross-linkable, curable polymer matrix that is permeable to oxygen. As in Example 1, Fluorolink™ B was used as the precursor to the cured perfluorinated urethane acrylate polymer which serves as the primary component of the polymer matrix. In this example, cure was effected with moisture.

Tris(4,7-diphenyl-1,10-phenanthroline)ruthenium(II) chloride (obtained from Florida International University) was selected as the oxygen sensitive indicator and N,N'-bis (2,5-di-tert-butylphenyl)-3,4,9,10-perylenecarboximide (DBPI) (Aldrich Chemical Co.) was selected as the reference dye. 1.5 mg each of DPPR and DBPI was dissolved in 0.2 ml $CH_2Cl_2$, and miscibilized in 1.0 g of the perfluorinated prepolymer Fluorolink™ B to which was added 10 μl dibutyltin dilaurate as a catalyst. Freon 113 trichlorotrifluoroethane (200 μl) was added and the solution was thoroughly mixed.

The waveguide (Ensign Bickford glass-on-glass, 240 μm, numerical aperture 0.39) was dipped in the polymer/oxygen indicator/reference dye preparation and allowed to dry at room temperature overnight. The dried sensor was cured at 50° C. in a humidified forced air oven for 18 hours.

EXAMPLE 3

The objective of this experiment was to determine the optimal wavelengths at which to excite an oxygen indicator dye and a reference dye, and at which wavelengths to monitor the fluorescence emission spectra. Either tris(4,7-diphenyl-1,10-phenanthroline)ruthenium(II) chloride or N,N'-bis(2,5-di-tert-butylphenyl)-3,4,9,10-perylenecarboximide (DBPI) (Aldrich Chemical Co.), or both DPPR and DBPI, was dissolved in methylene chloride at approximately 0.1 wt. %, miscibilized within the perfluorinated polyurethane prepolymer and cured in the standard fashions, either by moisture curing mechanisms or photo-curing the perfluorinated urethane acrylate prepolymer.

Figure 4:
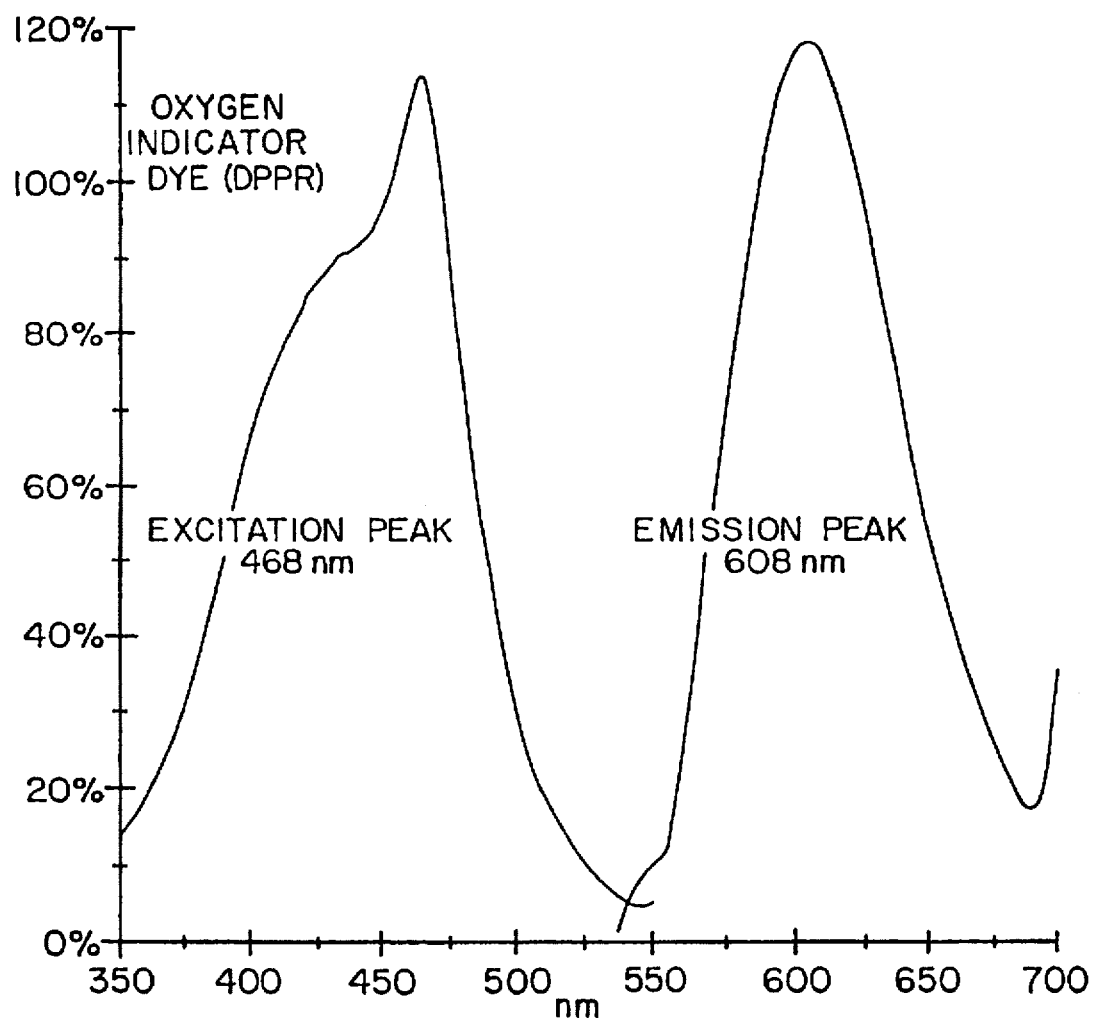
FIG. 4 shows the excitation and emission spectra of the oxygen indicator, tris(4,7-diphenyl-1,10-phenanthroline) ruthenium(II) chloride (also referred to as [Ru(4,7-Ph$_2$phen)$_3$] Cl$_2$ or DPPR) in a perfluorinated urethane polymer film, as evaluated in Example 3.
Figure 5:
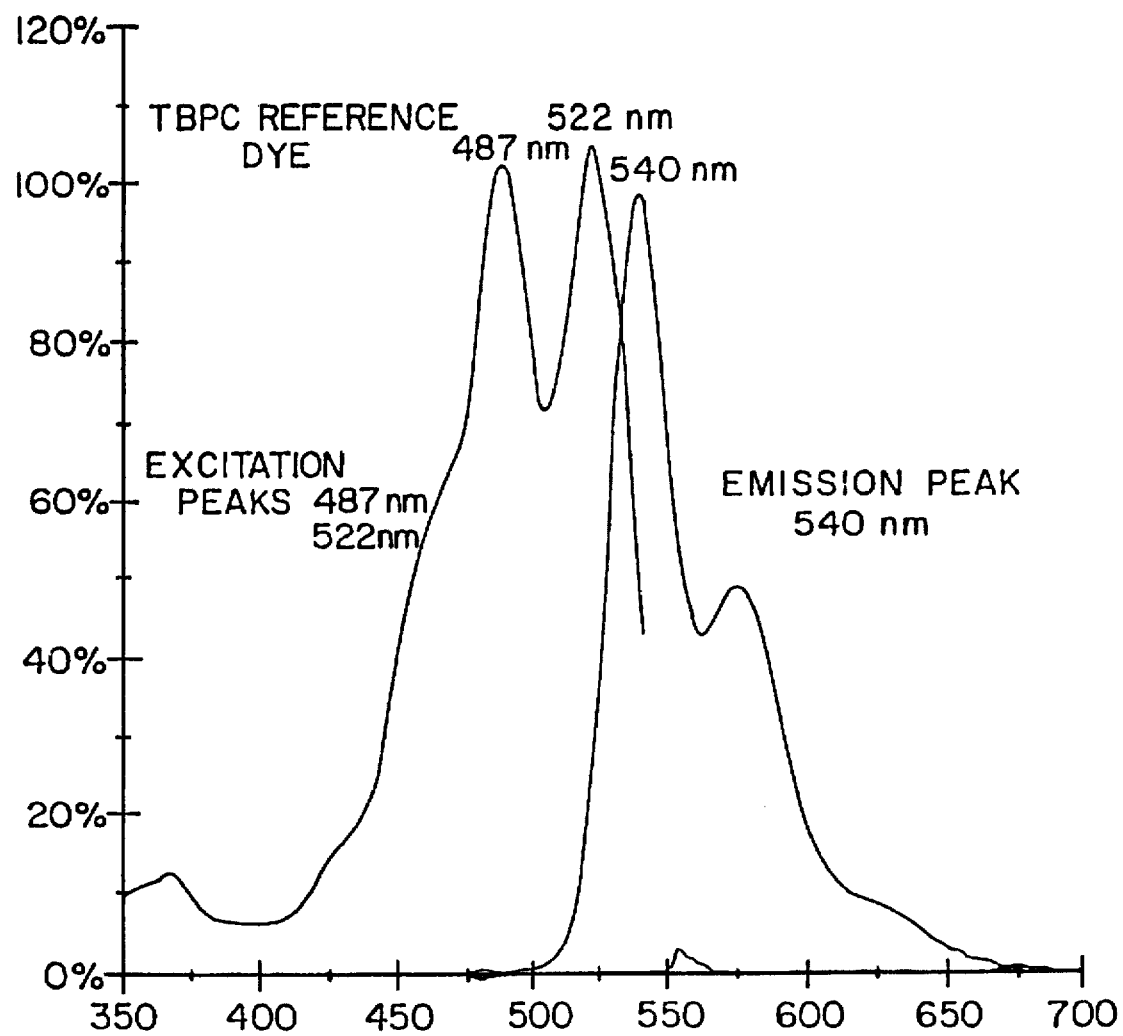
FIG. 5 shows the excitation and emission spectra of the reference dye, N,N'-bis(2,5-di-tert-butylphenyl)-3,4,9,10-perylenecarboximide, in a perfluorinated urethane polymer film, as evaluated in Example 3.
Figure 6:
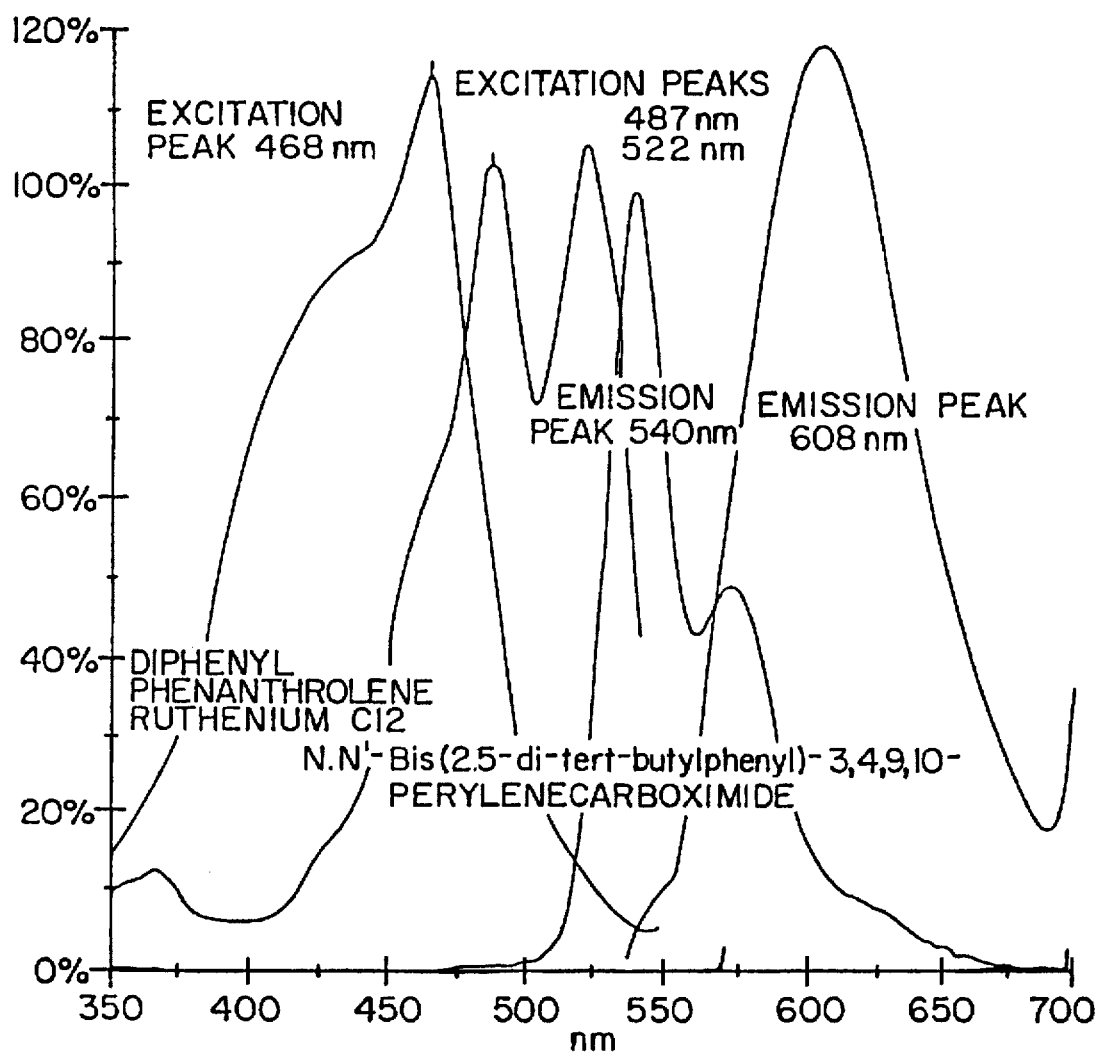
FIG. 6 shows the composite excitation and emission spectra of the oxygen indicator, tris(4,7-diphenyl-1,10-phenanthroline)ruthenium(II) chloride and the reference dye, N,N'-bis(2,5-di-tert-butylphenyl)-3,4,9,10-perylenecarboximide, in a single perfluorinated urethane polymer film, as evaluated in Example 3.

Films generated from this polymer-indicator or polymer-reference dye mixture have the following fluorescence spectrum. FIG. 4 shows the excitation and emission spectra of the oxygen indicator in the urethane film. FIG. 5 shows the excitation and emission spectra of the reference dye in the urethane film. FIG. 6 shows the excitation and emission spectra of the two compounds within the same urethane film. Note that one can excite both dyes at 485 nm and capture the oxygen emission signal at 607 nm and the reference compound signal at 540 nm, all of which are easily deconvolutable using conventional optical filters. Ratioing the signal at 607 nm to that at 540 nm yields the desired calibration ratio.

EXAMPLE 4

The purpose of this experiment was to evaluate DBPI as a reference dye for use with ruthenium oxygen indicator dyes. An optical sensor was prepared as described in Example 2, incorporating both DPPR and DBPI into the polymer matrix. The rate of photodrift was measured by exciting both the indicator and the reference dye at 485 nm, while the oxygen emission signal was captured at 607 nm and the reference compound signal at 540 nm. Ratioing the signal at 607 nm to that at 540 nm yielded the desired calibration ratio.

Figure 7:
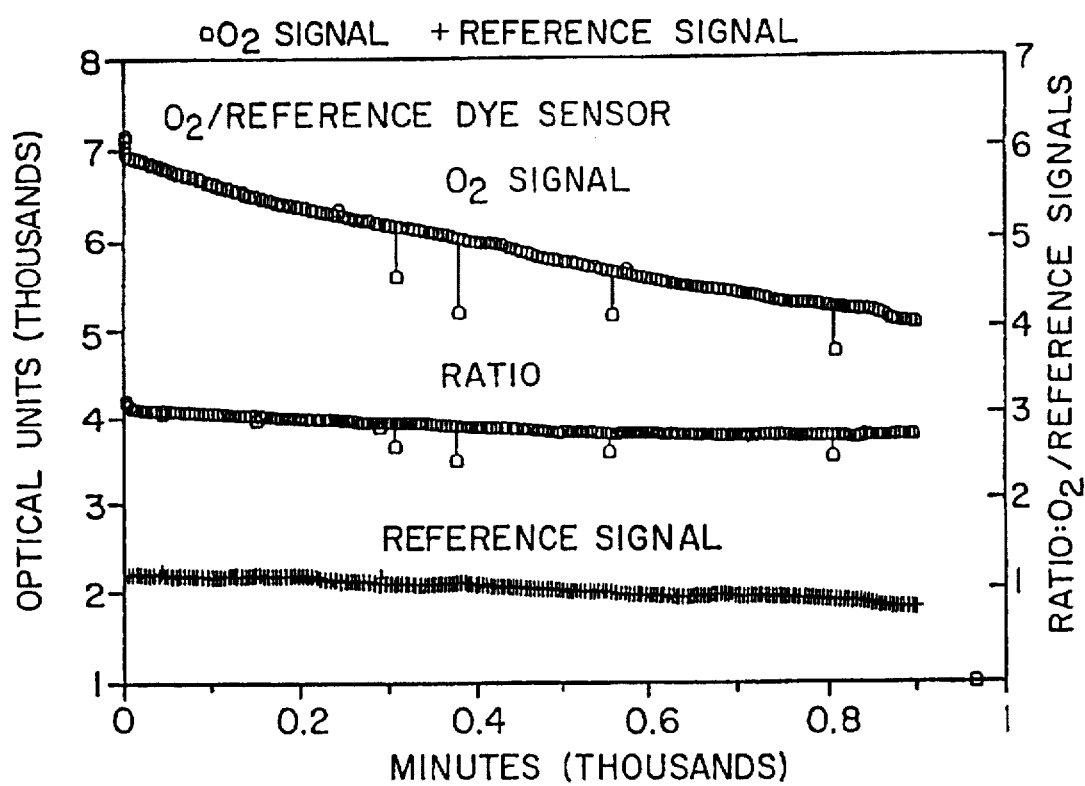
FIG. 7 show the results of a photo drift study of a typical optical oxygen sensor, as described in Example 4. Depicted in this Figure is the oxygen signal from tris(4,7-diphenyl-1,10-phenanthroline)ruthenium(II) chloride, the reference signal from N,N'-bis(2,5-di-tert-butylphenyl)-3,4,9,10-perylenecarboximide, and the ratio of the oxygen signal to the reference signal.

The results indicated that the rates of photodecomposition are constant and similar for the indicator dye and the reference dye with exposure to various concentrations of dissolved. FIG. 7 shows the results of a typical photo drift study. The unratioed decay rate is substantially greater than the ratioed sensor.

The drift rate and useful life of the sensor were compared by monitoring the signal from the oxygen indicator dye with the ratio of the signal from the oxygen indicator dye to the signal from the reference dye. The results shown in Table I indicate that the drift rate decreased by more than half and the useful life is more than doubled for the ratioed signal relative to the unratioed oxygen signal.

TABLE I

|  | $K_{sv}$* | DRIFT RATE | NEW $O_2$/HR | USEFUL LIFE (hours) |
| --- | --- | --- | --- | --- |
| SIGNAL ONLY | 0.012 | 1.8%/hr | 155 | 3.33 |
| RATIO | 0.008 | 0.8%/hr | 152 | 6.5 |

*Stern Volmer constant, in $mm^{-1}$

EXAMPLE 5

The object of this experiment was to evaluate the ratiometric method of the invention in an in vivo setting. Optical sensors were prepared as described in Example 2. Following standardization against solutions containing known amounts of dissolved oxygen, the sensors were surgically implanted in rabbits. The implanted sensors were continuously irradiated at 485 nm (the excitation wavelength) for 24 hours, after which the sensors were removed. The "explant" sensors were again standardized against solutions of dissolved oxygen as above.

Figure 8:
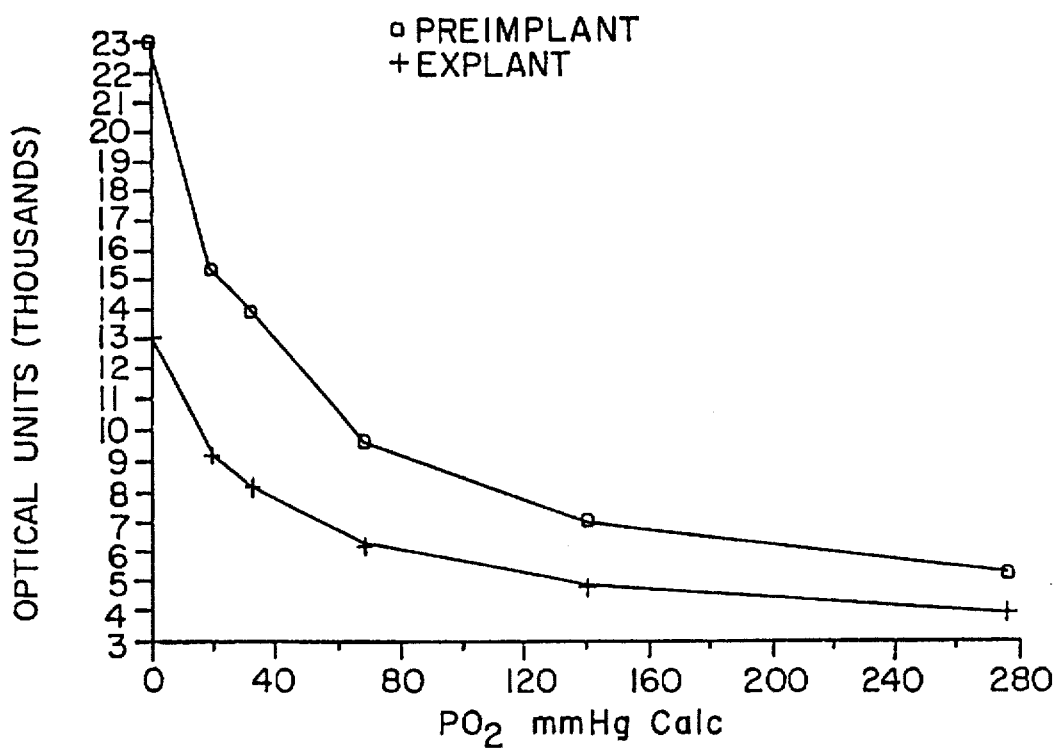
FIG. 8 shows the results of a 24-hour in vivo study with uncorrected oxygen sensor signals as evaluated in Example 5.
Figure 9:
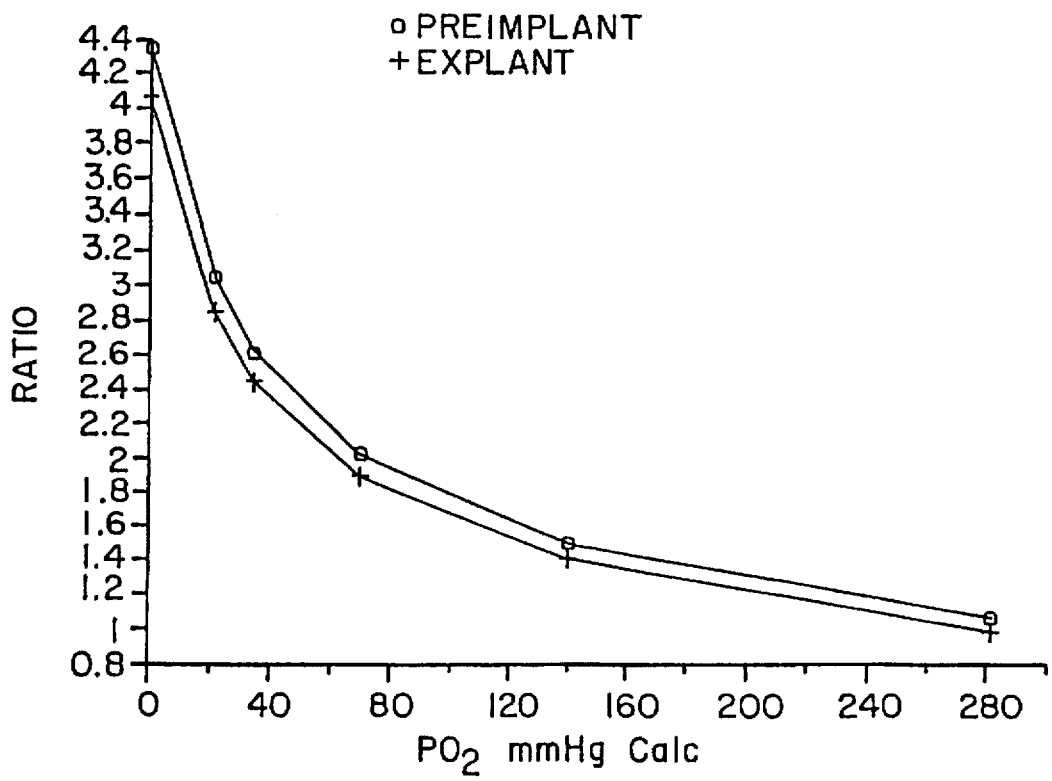
FIG. 9 shows the results of a 24-hour in vivo study with oxygen sensor signals ratioed as evaluated in Example 5.

FIGS. 8 and 9 show the results of a 24-hour in vivo study with sensors unratioed and ratioed, respectively. The drift in the standardization curve, and thus the relative instability of the sensor due to photodecomposition, can be observed in FIG. 8 by comparing the pre-implant signal with the explant signal. By comparison, FIG. 9 shows that the pre- and post-implant standardization curves are virtually superimposable reflecting the greater stability of the sensor operated. In this particular example, sensor life was extended approximately 110%.

We claim:

1. An optical sensor for measuring oxygen in a fluid sample, comprising an optical waveguide having a distal end portion for contacting the fluid, and a proximal end portion for communication with means for receiving a signal from the distal end portion, and wherein the distal end portion has an oxygen sensor means comprising a cross-linked oxygen-permeable membrane of a cured perfluorinated urethane polymer and, incorporated therein, an indicator composition comprising an oxygen indicator and a reference dye, wherein the oxygen indicator provides for an oxygen-sensitive fluorescence emission signal, and wherein the reference dye provides for an oxygen-insensitive fluorescence emission signal.

2. The optical sensor of claim 1, wherein the oxygen indicator is selected from the group consisting of complexes of ruthenium (II), osmium (II), iridium (III), rhodium, rhenium, and chromium (III) with 2,2'-bipyridine, 1,10-phenanthrolene, 4,7-diphenyl-1,10-phenanthrolene, 4,7-dimethyl-1,10-phenanthrolene, 4,7-disulfonated-diphenyl-1,10-phenanthrolene, 2,2'-bi-2-thiazoline, 2,2'-bithiazole, 5-bromo-1,10-phenanthrolene, and 5-chloro-1,10-phenanthrolene, and complexes of VO (II), Cu (II), platinum (II), and zinc (II) with porphyrin, etioporphyrin, tetraphenylporphyrin, mesoporphyrin IX dimethylester, protoporphyrin IX dimethylester and octaethylporphyrin.

3. The optical sensor of claim 1, wherein the reference dye is a fluorescent organic compound is selected from the group consisting of fluorescein, carboxyfluorescein, hydroxypyrene trisulfonic acid, dichlorofluorescein, N,N'-bis(2,5-di-tert-butylphenyl)-3,4,9,10-perylenecarboximide, and N,N'-bis(2,6-xylidyl)-3,4,9,10-perylenecarboximide.

4. The optical sensor of claim 1, wherein the oxygen indicator is tris(4,7-diphenyl-1,10-phenanthroline) ruthenium(II) chloride and the reference dye is selected from the group consisting of N,N'-bis(2,5-di-tert-butylphenyl)-3,4,9,10-perylenecarboximide and N,N'-bis(2,6-xylidyl)-3,4,9,10-perylenecarboximide.

5. The optical sensor of claim 1, wherein the cured perfluorinated urethane polymer comprises a perfluorinated urethane polymer precursor cross-linked with a cross-linking agent.

6. The optical sensor of claim 5, wherein the perfluorinated urethane polymer precursor has the structural formula

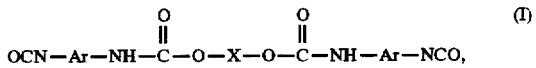

wherein Ar is a monocyclic aromatic moiety and X is a perfluorinated polyether linkage containing approximately 2 to 100 recurring perfluorinated monomer units having the structure (—$CF_2O$—), (—$CF_2CF_2O$—), or combinations thereof.

7. The optical sensor of claim 6, wherein the cross-linking agent is water.

8. The optical sensor of claim 6, wherein the cross-linking agent is a diol.

9. The optical sensor of claim 1, wherein the cured perfluorinated urethane polymer comprises a perfluorinated urethane polymer precursor having the structural formula

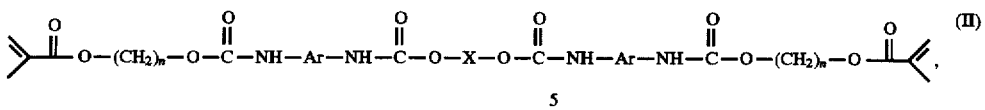

wherein Ar is a monocyclic aromatic moiety, X is a perfluorinated polyether linkage containing approximately 2 to 100 recurring perfluorinated monomer units having the structure (—$CF_2O$—), (—$CF_2CF_2O$—), or combinations thereof, and n is an integer in the range of 0 to 6 inclusive, and wherein the precursor is cured with a photoinitiator in the presence of radiation.

10. The optical sensor of claim 1, wherein the cured perfluorinated urethane polymer comprises an epoxy-terminated precursor having the structural formula

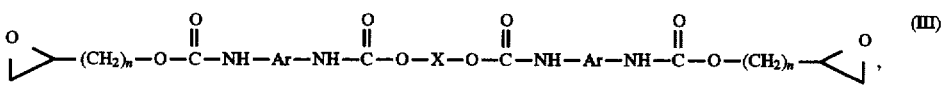

wherein Ar is a monocyclic aromatic moiety, X is a perfluorinated polyether linkage containing approximately 2 to 100 recurring perfluorinated monomer units having the structure (—$CF_2O$—), (—$CF_2CF_2O$—), or combinations thereof, and n is an integer in the range of 0 to 6 inclusive, and wherein the precursor is cured with a photoinitiator in the presence of radiation.

* * * * *